US008092548B2

(12) United States Patent
McKay et al.

(10) Patent No.: US 8,092,548 B2
(45) Date of Patent: Jan. 10, 2012

(54) OSTEOGRAFT TREATMENT TO PROMOTE OSTEOINDUCTION AND OSTEOGRAFT INCORPORATION

(75) Inventors: William F. McKay, Memphis, TN (US); John M. Zanella, Cordova, TN (US); Jeffrey M. Gross, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1266 days.

(21) Appl. No.: 11/158,924

(22) Filed: Jun. 22, 2005

(65) Prior Publication Data
US 2006/0293757 A1    Dec. 28, 2006

(51) Int. Cl.
*A61F 2/28* (2006.01)
(52) U.S. Cl. .................. 623/23.55; 623/16.11
(58) Field of Classification Search .... 623/17.11–17.16, 623/16.11, 23.55
See application file for complete search history.

(56) References Cited

U.S. PATENT DOCUMENTS

| | | | |
|---|---|---|---|
| 4,950,296 A | | 8/1990 | McIntyre |
| 5,769,897 A | * | 6/1998 | Harle ............................ 424/423 |
| 6,039,762 A | * | 3/2000 | McKay ..................... 623/17.11 |
| 2002/0082694 A1 | | 6/2002 | McKay |
| 2002/0173851 A1 | | 11/2002 | McKay |
| 2003/0195629 A1 | | 10/2003 | Pafford et al. |
| 2004/0034428 A1 | | 2/2004 | McKay |
| 2004/0082937 A1 | | 4/2004 | Ausiello et al. |
| 2005/0004672 A1 | | 1/2005 | Pafford et al. |
| 2005/0031666 A1 | | 2/2005 | Trieu |
| 2005/0130301 A1 | | 6/2005 | McKay et al. |
| 2005/0192669 A1 | | 9/2005 | Zdeblick et al. |
| 2006/0093646 A1 | * | 5/2006 | Cima et al. .................... 424/425 |

* cited by examiner

*Primary Examiner* — Bruce E Snow

(57) ABSTRACT

The invention provides a bone implant, or osteograft, with improved retention of bioactive agents within the surface of the osteograft. Pits or pits formed within the surface of the osteograft have porous plugs placed within them to retain fluid comprising bioactive agents. Pits can also be formed so that the dimensions of the pits facilitate retention of fluid within a pit by hydrostatic attraction of fluid molecules within the pit.

13 Claims, 10 Drawing Sheets

1a

1b

1c

1d

1a

1b

1c

1d

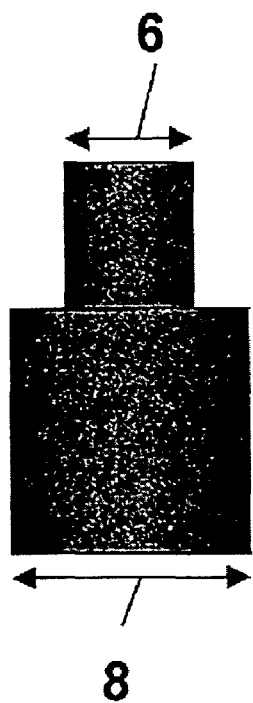
FIG. 2A
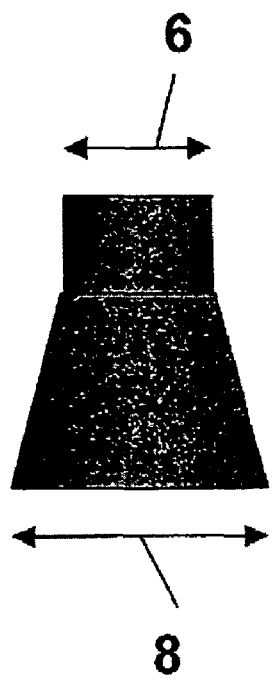
FIG. 2B
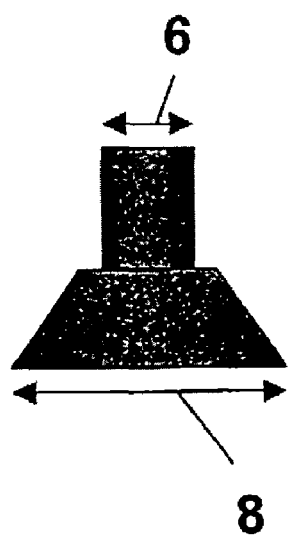
FIG. 2C
FIG. 2

OSTEOGRAFT TREATMENT TO PROMOTE OSTEOINDUCTION AND OSTEOGRAFT INCORPORATION

FIELD OF THE INVENTION

The present invention relates generally to bone grafts and methods for preparing graft materials. The invention also relates to implants, for example, implants suitable for insertion into the intervertebral space and to implants suitable for use in orthopedic applications.

BACKGROUND OF THE INVENTION

Bone grafts are used to repair bone that has been damaged by disease, trauma, or surgery. Grafts may be utilized when healing is impaired in the presence of certain drugs or in disease states such as diabetes, when a large amount of bone or disc material is removed during surgery, or when bone fusion is needed to create stability. In some types of spinal fusion, for example, bone grafts are used to replace the cushioning disc material between the vertebrae.

Bone graft (osteograft) materials may include both synthetic and natural bone. Natural bone may be taken from the graft recipient (autograft) or may be taken from another source (allograft), such as a cadaver, or (xenograft), such as bovine. Autograft has advantages such as decreased immunogenicity and greater osteoinductive potential, but there can also be problems with donor site morbidity and limited supply of suitable bone for grafting. On the other hand, allograft is available in greater supply and can be stored for years—but is less osteoinductive.

Osteoconduction and osteoinduction both contribute to bone formation. A graft material is osteoconductive if it provides a structural framework or microscopic and macroscopic scaffolding for cells and cellular materials that are involved in bone formation (e.g., osteoclasts, osteoblasts, vasculature, mesenchymal cells). Osteoinductive material, on the other hand, stimulates differentiation of host mesenchymal cells into chondroblasts and osteoblasts. Natural bone allograft materials can comprise either cortical or cancellous bone. A distinguishing feature of cancellous bone is its high level of porosity relative to that of cortical bone, providing more free surfaces and more of the cellular constituents that are retained on these surfaces. It provides both an osteoinductive and osteoconductive graft material, but generally does not have significant load-bearing capacity. Optimal enhancement of bone formation is generally thought to require a minimum threshold quantity of cancellous bone, however. Cortical (compact) bone has greater strength or load-bearing capacity than cancellous bone, but is less osteoconductive. In humans for example, only twenty percent of large cortical allografts are completely incorporated at five years. Delayed or incomplete incorporation may allow micromotion, leading to host bone resorption around the allograft. A more optimal bone graft material would combine significant load-bearing capacity with both osteoinductive and osteoconductive properties, and much effort has been directed toward developing such a graft material.

Some allografts comprise mammalian cadaver bone treated to remove all soft tissue, including marrow and blood, and then textured to form a multiplicity of holes of selected size, spacing, and depth. The textured bone section is then immersed and demineralized, preferably in a dilute acid bath. Demineralizing the bone exposes osteoinductive factors, but extensive demineralization of bone also decreases its mechanical strength.

Allograft has also been formed of organic bone matrix with perforations that extend from one surface, through the matrix, to the other surface to provide continuous channels between opposite surfaces. The organic bone matrix is produced by partial or complete demineralization of natural bone. Although the perforations increase the scaffolding potential of the graft material and may be filled with osteoinductive material as well, perforating organic bone matrix through the entire diameter of the graft decreases its load-bearing capacity.

Partially-demineralized cortical bone constructs may be surface-demineralized to prepare the graft to be soaked in bone growth-promoting substances such as bone morphogenetic protein (BMP). Although this design allows greater exposure of the surrounding tissue to growth-promoting factors, the surface demineralization necessary to adhere a substantial amount of growth-promoting factors to the graft material decreases the allograft's mechanical strength. Demineralized bone allograft materials are commercially available and widely used, since demineralization exposes underlying BMP at the surface of the allograft, but these materials lack the mechanical strength necessary to provide an optimal bone graft material and the treatment does not result in exposure of enough BMP to be of significant benefit in promoting osteoinduction.

What is needed is a bone graft material that combines the osteoinductive and osteoconductive properties of cancellous bone with the load-bearing capacity provided by cortical allograft materials.

SUMMARY OF THE INVENTION

The invention provides a bone graft material ("osteograft") that retains bioactive agents to facilitate host bone incorporation while maintaining load-bearing capacity, the osteograft having at least one pit in at least one surface of the osteograft, and at least one plug inserted into the pit. The plug may be formed of one or more porous materials. In one embodiment, the plug can comprise cancellous bone. In other embodiments, plugs may be formed of a variety of natural or synthetic materials, or a combination of both.

The invention also provides a method of constructing an osteograft that retains bioactive agents, the method comprising forming at least one pit in at least one surface of an osteograft, and forming a plug to insert into the pit.

The invention also provides a method for decreasing incorporation time for implanted osteograft, by forming at least one pit in at least one surface of the osteograft and inserting a biologic or non-biologic plug into the pit to absorb and retain the bioactive agent within the pit, forming the pit to have a shape that increases retention of the bioactive agent through hydrostatic attraction, or a combination of both.

Bioactive agents may also be retained by an osteograft described by the present invention when one or more pits are formed in a shape that provides increased hydrostatic attraction of the fluid retained within the pit. Plugs may or may not be inserted into such pits, since the shape of the pit promotes fluid retention whether a plug is present or not.

Also provided by the invention are bone graft systems or kits comprising osteografts having pits formed in one or more surfaces of the osteograft, and plugs for insertion into the pits or plugs already inserted into one or more pits. Such kits may also comprise aliquots of bioactive agents suitable for application to the osteograft pits.

BRIEF DESCRIPTION OF THE DRAWINGS

FIG. 2A illustrates side views pit shapes that retain fluid by hydrostatic attraction of fluid within the pit. Such pits typically, but not necessarily, have an opening diameter 6 that is less than the base diameter 8 of the pit.

FIG. 2B illustrates side views pit shapes that retain fluid by hydrostatic attraction of fluid within the pit. Such pits typically, but not necessarily, have an opening diameter 6 that is less than the base diameter 8 of the pit.

FIG. 2C illustrates side views pit shapes that retain fluid by hydrostatic attraction of fluid within the pit. Such pits typically, but not necessarily, have an opening diameter 6 that is less than the base diameter 8 of the pit.

DETAILED DESCRIPTION

Figure 1:
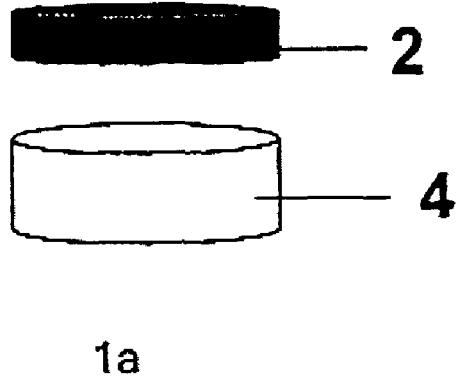
FIG. 1a illustrates lateral cross-sectional views of pits 4 and corresponding plugs 2 of complementary geometric shape that may be provided in an osteograft as described by the present invention.
FIG. 1b illustrates lateral cross-sectional views of pits 4 and corresponding plugs 2 of complementary geometric shape that may be provided in an osteograft as described by the present invention.
FIG. 1c illustrates lateral cross-sectional views of pits 4 and corresponding plugs 2 of complementary geometric shape that may be provided in an osteograft as described by the present invention.
FIG. 1d illustrates lateral cross-sectional views of pits 4 and corresponding plugs 2 of complementary geometric shape that may be provided in an osteograft as described by the present invention.
Figure 1:
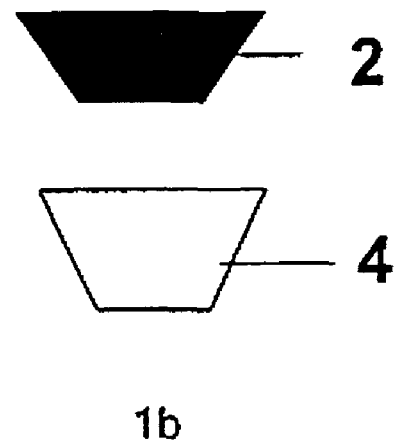
Figure 1:
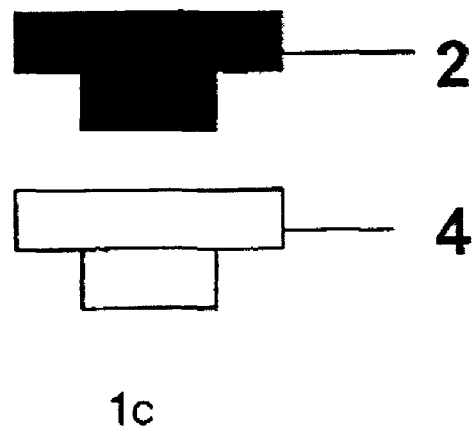
Figure 1:
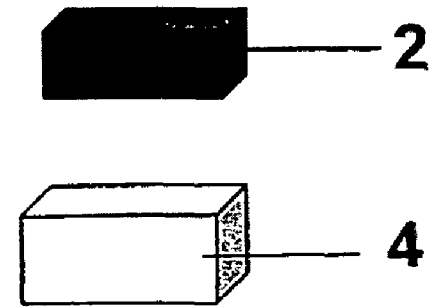

The inventors have discovered that cortical allograft or synthetic bone material can be utilized to form a bone graft material ("osteograft") that combines osteoinductive and osteoconductive properties with load-bearing capacity. An osteograft of the invention incorporates the beneficial properties of cancellous bone but retains the superior load-bearing capacity of cortical bone. As used herein, "osteograft" encompasses natural bone allograft such as cortical bone, synthetic materials used to form bone graft substitutes, and combinations of natural and synthetic materials. Synthetic materials suitable for allograft formation include, for example, coralline hydroxyapatite, tricalcium phosphate and hydroxyapatite, calcium sulfate, Bioglass® granules (Novabone Products, Alachua, Fla.), alpha-tricalcium phosphates, calcium carbonate, and a variety of ceramic materials. The invention provides an osteograft that provides faster, more uniform fusion, a more uniform outcome, and the potential for less pain, than that provided by allograft or synthetic graft materials currently in orthopedic use. An osteograft of the invention may comprise allograft or xenograft material.

An osteograft as described by the invention has load-bearing properties provided by natural allograft or synthetic bone in conjunction with osteoinductive properties provided by pits formed in the osteograft to not only increase surface area but also to make bioactive agents available at the graft/host junction. Bioactive agents may be osteoinductive factors. These agents are retained within the osteograft pits by plugs inserted into the pits or by forming the pits to increase fluid retention through hydrostatic force within the pit, or a combination of both.

The invention also provides a method for retaining a bioactive agent in an implanted osteograft. "A bioactive agent," as used herein, encompasses one or a combination of two or more bioactive factors such as, for example, bone-growth promoting cellular factors such as bone morphogenetic protein (BMP), LIM mineralization protein (LMP), particulate bone, CHRYSALIN®, bone marrow aspirate, concentrated bone marrow aspirate, and demineralized bone matrix (DBM), growth differentiation factor, such as GDF-5, anti-inflammatory factors such as TNF inhibitors, anti-infective agents, mesenchymal cells, hematopoietic cells, osteogenic precursor cells, or various types of stem cells, pain relief agents, or a combination thereof. Non-polymeric hematopoietic cell clots, for example, such as those described by Pascher, et al., U.S. patent application Ser. No. 10/457,000 (Publication No. 20040037819) may be useful as bioactive agents, and for delivery of bioactive agents, in an osteograft of the invention. A variety of bioactive agents known to those of skill in the art are suitable for use in the osteograft and method of the present invention.

Bioactive agents can be provided in modified release form such as, for example, polymers in formulation with one or more bioactive agents to control the rate of dissolution or diffusion of the agent, functional coatings to delay dissolution or release of bioactive agents, or other similar compositions such as modified-release microspheres known to those of skill in the art. References such as the *Handbook on Pharmaceutical Controlled Release Technology*, D. L. Wise (ed.), Marcel Dekker, Inc., New York (2000) provide examples and instruction for formulating modified release compositions appropriate for use in the present invention.

The invention provides an osteograft and method that increase the amount of at least one bioactive agent, such as BMP, available at the osteograft/host bone junction and thereby decrease the time required for osteograft incorporation. Allografts inserted without the addition of BMP generally take 12 to 18 months for incorporation. When BMP is available at the junction between the allograft and the host bone endplates, the time for incorporation can be cut by one-third to one-half. Faster incorporation and fusion of bone in spine fusion can decrease undesirable motion along the allograft/host end plate interface.

As used herein, a "pit" is a defined space formed beneath at least one surface of an osteograft or an area sunken or depressed below the adjacent osteograft surface, and the term can be used interchangeably with the terms "depression," "cavity," "indentation," "hollow," or "hole." Pits may be formed in various dimensions and shapes, such as about 2 mm in diameter and about 3 mm in depth, or about 1 mm in diameter and about 1 mm in depth. Generally, it may be beneficial to form a pit so that the ratio of depth to diameter is at least about 2 to 1 to promote retention of fluid within the pit. Pits may also be formed so that the opening is wider than the base to more easily insert plugs, or so that the base is wider than the opening to increase retention of the plug or retention of fluid within the pit through hydrostatic forces. Dimensions chosen for depth and diameter of the pits should increase exposure to osteoinductive factors at the surface of the allograft, while maintaining the structural integrity and load-bearing capacity of the allograft.

Pits can be formed in an osteograft as it is formed of synthetic materials. The desired pattern and shape of pits can also be formed in an osteograft "blank" formed of natural allograft or synthetic material. Pits may be formed by means known to those of skill in the art such as, for example, laser drilling, mechanical drilling, computer-numerically-controlled (CNC) milling, and press-forming. Pits can be formed in uniform or non-uniform cross-sectional shape, can be circular, semi-circular, conical, rectangular, or cylindrical with a conical portion (particularly at the base), for example. Pits may be axisymetric or asymmetric.

Appropriate shape(s) for pits in a particular osteograft can be determined by those of skill in the art. Pit density and diameter, as well as pit depth, should be chosen according to the desired location and requisite load-bearing capacity of the allograft. The inventors recommend, for example, that the diameter of individual pits be minimized in osteografts needed for heavier load-bearing uses. Larger pits (in terms of depth and diameter), can be utilized at the surfaces that will interface with the host bone, while smaller pits can be located elsewhere in the osteograft. Structural integrity and load-bearing capacity of the osteograft should be considered when determining the depth of the pits. It is generally not desirable to utilize pits that traverse the entire diameter of (i.e., "run through") the osteograft or have such depth that they may significantly decrease the load-bearing capacity of the osteograft.

Pits are especially beneficial on the surfaces where the host bone and osteograft make contact, since one goal of osteograft implantation is that the host bone grows into the pits. As the host bone expands into the pits, osteoblasts add new bone while osteoclasts remove the osteograft bone material. Through "creeping substitution," the osteograft becomes incorporated and eventually replaced by host bone tissue.

Figure 4:
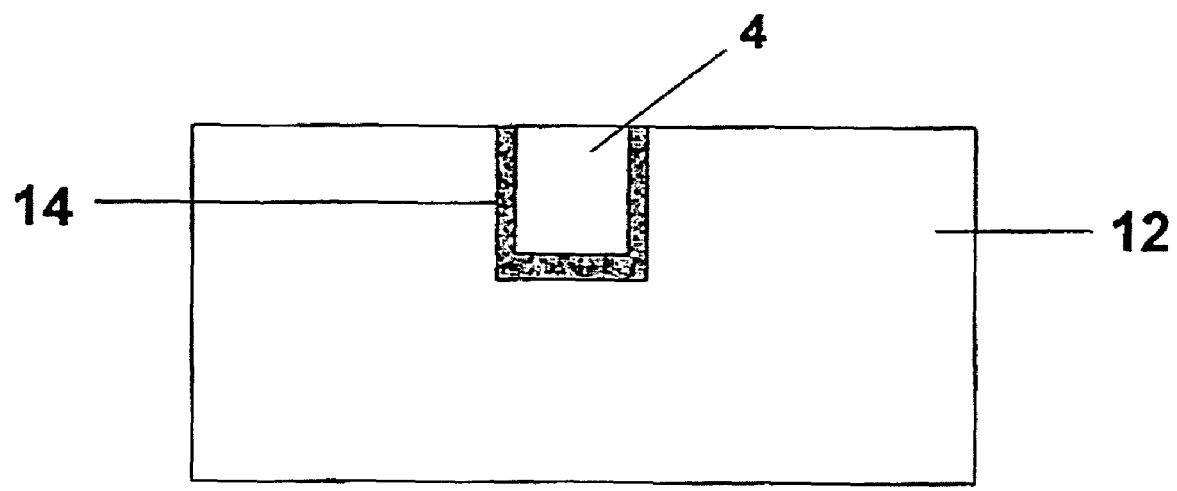
FIG. 4 is a cross-sectional view of an embodiment of an osteograft 12 as described by the invention wherein at least one internal surface of a pit 4 is demineralized to form a zone of demineralization 14.

The interior of one or more pits may be treated to demineralize the interior surface of the pit, as shown in FIG. 4, which illustrates a pit 4 having a zone of demineralization 14 along its internal surface(s). Pits can be demineralized, for example, by applying hydrochloric acid (e.g., 0.6 M HCl) within them and then rinsing the acid from the pit. The extent of demineralization of pits should be limited so that it is not so significant as to affect the structural integrity and load-bearing capacity of the allograft.

Figure 3:
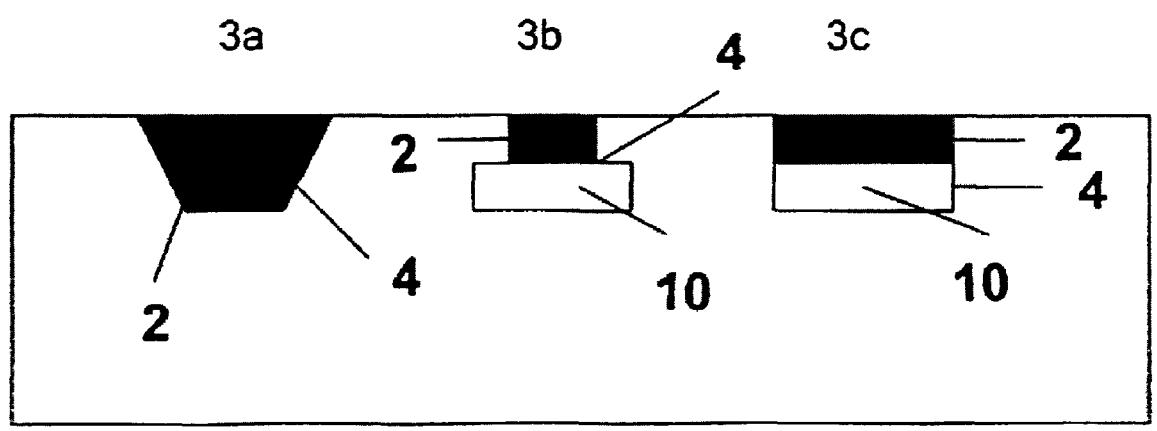
FIG. 3 illustrates cross-sectional views of alternate embodiments of pit 2 and plug 4 combinations in an osteograft 12 according to the invention. In 3a, a pit 4 is substantially filled by plug 2. In 3b, a reservoir 10 is created between plug 2 and pit 4 when plug 2 is placed into pit 4 so that it fits within the opening of the pit but does not fill the pit. Rather, placement of the plug in the opening leaves a space for fluid between the plug and the bottom and side(s) of the pit, forming the reservoir. In 3c, a plug 2 is placed into a pit 4 of similar geometry so that a reservoir is formed.

In one embodiment of the invention plugs formed of porous material can be placed within one or more pits formed in an osteograft. "Porous" plugs are plugs having sufficient permeability or porosity to absorb or adsorb at least a minimal quantity of fluid, paste, or putty comprising at least one bioactive substance. As shown in FIG. 1A-FIG. 1D, pits 4 of various geometries can be formed in an osteograft of the present invention and can have plugs 2 of complementary geometry, as shown, inserted therein. In one embodiment of the invention, a plug 2 essentially fills a pit 4 (FIG. 3A). In another embodiment, a plug can be placed into a pit so that a space is formed between the bottom of the plug and the bottom of the pit to create a reservoir 10 between the plug and the bottom and side(s) of the pit, as shown in FIG. 3B and FIG. 3C. Plugs may be complementary in shape to a corresponding pit, may be irregular in shape, may be formed in the shape of a wedge, cylinder, or ellipse, for example, and may have curved, linear, or other surfaces that are appropriate for the design of the individual type of plug. One plug or more than one plug may be placed within any one pit.

Plugs can be made of biologic or non-biologic material, including porous synthetic materials, cancellous bone, porous collagen, gelatin, hyaluronic acid, cellulose, starch, calcium phosphate, or a combination thereof. Plugs may be formed from autograft, allograft or xenograft material.

Plugs may be placed into liquids comprising bioactive agents so that they will absorb such agents prior to being placed into the osteograft pits, or the osteograft may be placed in one or more bioactive agents after one or more plugs are placed in pits. Pits can be filled with bioactive agents prior to final assembly of the osteograft, or may be filled in the operating room prior to surgical implantation of the osteograft. Plugs can be used to provide a porous seal for a reservoir provided by the pit (FIG. 3B and 3C), or can fill the pit (FIG. 3A) to retain a bioactive agent. Plugs may be inserted into pits without a bioactive agent having been first applied, or a bioactive agent can be applied prior to inserting a plug into a pit. Bioactive agents may be applied to plugs by soaking the plugs in the agent, using a syringe or other applicator so that the bioactive agent can be absorbed by, or adsorbed to, the plug(s) before or after they are placed into pits, or other means known to those of skill in the art. Pastes, putties, or other compositions may also be spread along the allograft so that they fill a pit prior to or after insertion of one or more plugs.

Plugs may be inserted so that the top of the plug is flush with the surface of the allograft or so that it is depressed below the allograft surface.

In one embodiment of the invention, pits are formed so that the shape of a pit decreases the fluid force on the pit opening and increases retention of fluid placed within the pit. Such pits retain bioactive agents within them with or without plugs. FIG. 2 illustrates pits having shapes that increase fluid retention. Such pits can be created by those of skill in the art using various means such as, for example, a ball end mill of appropriate size. These pits generally have an opening with a diameter 10 that is less than the diameter of the base of the pit 12. When inverted so that the force of gravity pushes the fluid within the column against the pit opening, the force applied is based upon the diameter of the column of fluid directly over the opening, not upon the entire mass of fluid within the pit.

Pit shape and dimensions to increase hydrostatic pressure and surface tension within the pit can be determined by those of skill in the art, keeping in mind that if the net weight of fluid above the entrance to the pit is less than the fluid tension force acting at the pit entrance, the fluid will generally be retained inside the pit when the pit is inverted. The surface tension and density of a fluid having unknown surface tension and density can be experimentally determined by those of skill in the art without undue experimentation. Once these are determined, the pit dimensions can be calculated using:

$$W < \pi \cdot d \cdot \gamma$$

$$P \cdot A < \pi \cdot d \cdot \gamma$$

$$(\rho \cdot g \cdot h) \cdot \left(\frac{\pi \cdot d^2}{4}\right) < \pi \cdot d \cdot \gamma$$

$$d < \frac{4 \cdot \gamma}{\rho \cdot g \cdot h}$$

where:
W=weight of fluid column above the entrance to the pit, (dyne)
d=diameter of the projected column of fluid above the pit entrance, (cm)
A=cross-sectional area of the pit based on the diameter at the pit entrance, (cm$^2$)
p=density of the fluid contained in the pit, (g/cm$^3$)
γ=surface tension of the fluid contained in the pit, (dyne/cm)
g=gravitational constant, (cm/sec$^2$)
h=height of the fluid column, (cm)

Figure 5:
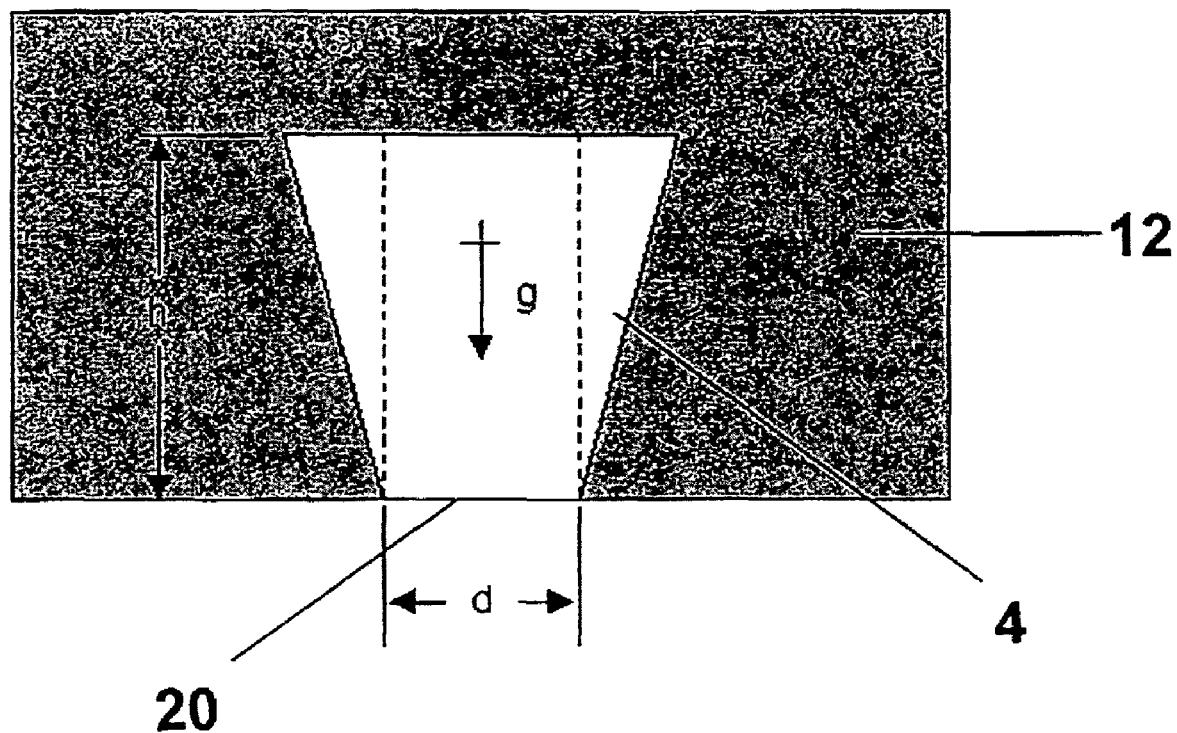
FIG. 5 illustrates the relationship between pit height, the diameter of the pit opening, and the surface tension of selected fluids (saline, water, bone marrow aspirate (BMA), bone morphogenetic protein (BMP-2)) within the pit. For a given fluid, the surface tension will hold the fluid in the pit when oriented downward if the diameter/height ratio of the pit is below the curve.
Figure 6:
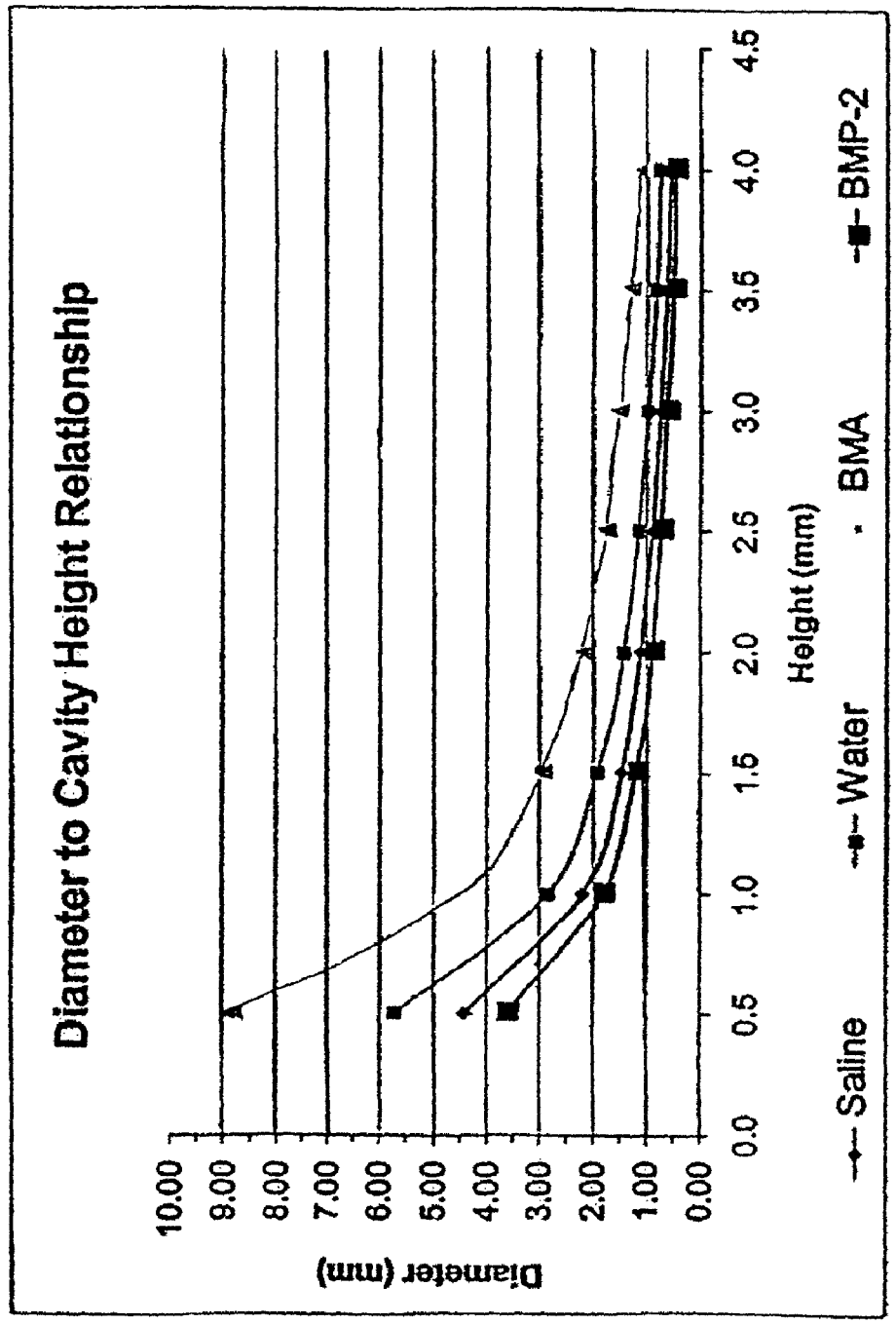
FIG. 6 is a graph indicting the Diameter to Cavity Height Relationship for saline, water, BMA and BMP-2.
Figure 7A:
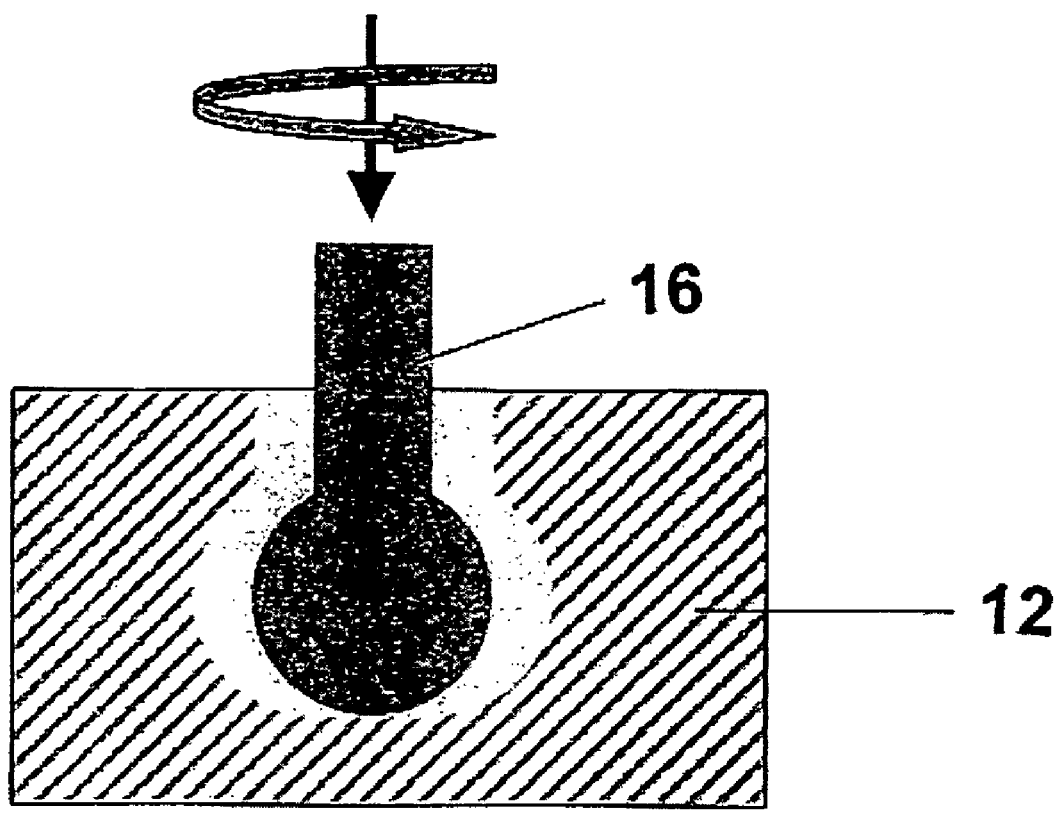
FIG. 7A is an illustration of a method for forming a pit 4 in an osteograft 12 by drilling or grinding with an implement such as a ball end mill 16. As the arrows indicate, the implement may be forced downward longitudinally as it rotates laterally. A variety of shapes can be achieved using such an implement and method. One such shape is shown in FIG. 7B.
Figure 7B:
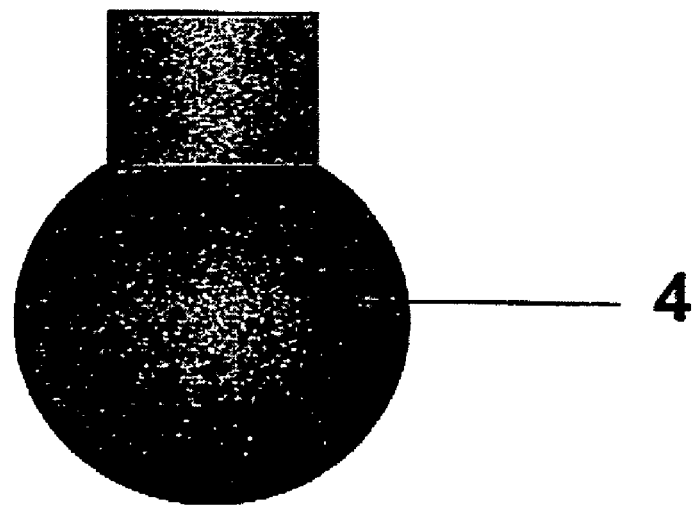
Figure 8A:
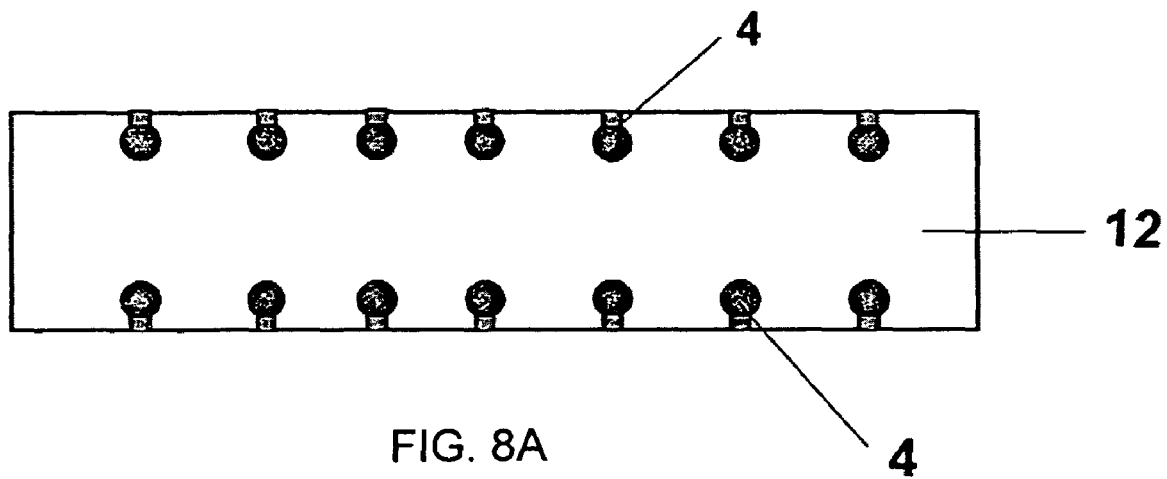
FIG. 8A is a cross-section of an osteograft 12 of the invention with pits 4 formed in two surfaces.
Figure 8B:
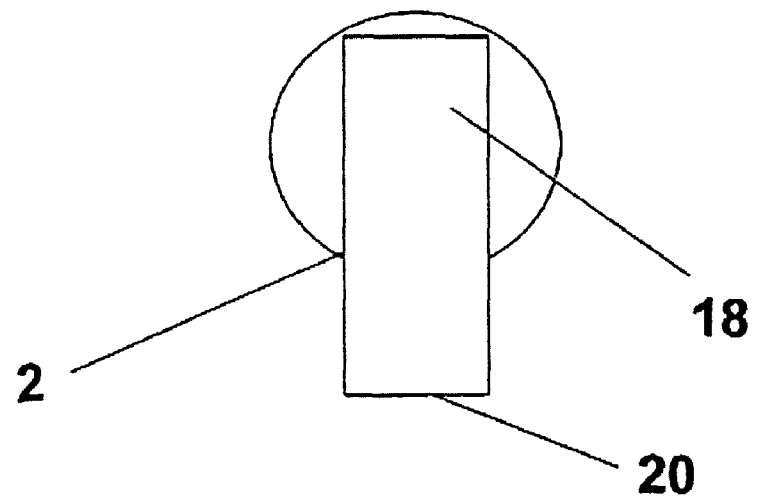
FIG. 8b is an inverted cross-section of a pit 4 as found in an osteograft 12 of the invention, fluid in the pit 2 forming a column 18 directly above the opening 6 of the pit.

Using these factors, the relationship of pit diameter to pit height can be graphed as in FIG. 5, where, if the diameter/height ratio of the pit is located in the area below the curve for a given fluid, surface tension will hold the fluid in the pit when the pit opening is oriented downward.

The invention may be further described by reference to the following non-limiting examples:

EXEMPLIFICATION

Example 1

A study was performed to screen allograft constructs using an ovine cortical defect model. Different allograft formations were compared using histomorphometric, histopathological, and biomechanical methods. Histopathologically and histomorphometrically, the combination of BMP and allograft surface depressions (ASD) showed synergistic effects to enhance bone remodeling and integration between host and graft tissues. The project scope involved undecalcified histological processing and biomechanical testing of 4 mm diameter defects created in ovine tibiae and metatarsals filled with allograft constructs. Six different allograft treatments were evaluated as detailed in Table 1.

TABLE 1

|  | #447 | #448 | #449 | #450 | #451 | #452 | #453 | #454 |
|---|---|---|---|---|---|---|---|---|
| Tibia |  |  |  |  |  |  |  |  |
| Very Proximal | Allograft | SDM + BMP | ASD | Allograft | SDM + BMP | ASD | Allograft | Xenograft |
| Proximal | SDM + BMP | ASD | Allograft | SDM + BMP | ASD | Allograft | SDM + BMP | xenograft |
| Distal | ASD | Allograft | SDM + BMP | ASD | Allograft | SDM + BMP | ASD | xenograft |
| Very Distal | Allograft | SDM + BMP | ASD | Allograft | SDM + BMP | ASD | No implant | xenograft |
| Metatarsals |  |  |  |  |  |  |  |  |
| Very Proximal | ASD + DBM | SDM | ASD + BMP | ASD + DBM | SDM | ASD + BMP | ASD + DBM | xenograft |
| Proximal | SDM | ASD + BMP | ASD + DBM | SDM | ASD + BMP | ASD + DBM | SDM | xenograft |
| Distal | ASD + BMP | ASD + DBM | SDM | ASD + BMP | ASD + DBM | SDM | ASD + BMP | xenograft |
| Very Distal | ASD + DBM | SDM | ASD + BMP | No implant | SDM | ASD + BMP | ASD + DBM | Xenograft |

Key:
SDM: Surface Demineralized Allograft;
ASD: Allograft with Surface Depressions;
SDM + BMP: Surface Demineralized All graft + rhBMP-2;
ASD + BMP: Allograft with Surface Depressions + rhBMP-2;
ASD + DBM: Allograft with Surface Depressions + Demineralized Bone Matrix Briefly, eight unilateral 4 mm diameter defects were created in the tibia and metatarsal bone of sheep. Designations for the defect location within the cortical bone were abbreviated according to the following scheme: very proximal tibia (t-vp), proximal tibia (t-p), distal tibia (t-d), very distal tibia (t-vd), very proximal metatarsal (m-vp), proximal metatarsal (m-p), distal metatarsal (m-d), and very distal metatarsal (m-vd). Eight sheep received eight defects each. Table 1 presents the assignment of each defect to biomechanics or histological evaluation.

Sample Preparation

Tibia and metatarsal bones from euthanized sheep were labeled and transported from necropsy to the Orthopaedic Bioengineering Research Lab (Colorado State University, Fort Collins, Colo.). Both an intro-operative surgical marker and inspection visually identified the defects. Defects and surrounding bone were carefully dissected using an Exakt Bone Saw (Exakt Technologies, Oklahoma City, Okla.). For defects undergoing biomechanical testing, every effort was made to retain 4-5 cm of host bone for purposes of mounting and orientation in the testing fixture. For histological specimens, no more than 1 cm of bone surrounding the defect was retained. Each specimen, biomechanical and histological, was radiographed in both sagittal and coronal orientations.

Undecalcified Histology

Trimmed samples were fixed by soaking in 70% ethyl alcohol (ETOH) for 1 week. The specimens were dehydrated in graded solutions of ETOH (70%, 95%, and 100%) over the course of approximately 3 weeks with increasing concentrations of Technovit 7000 (embedding resin). The final solution contained 100% of the embedding resin and was polymerized using light activation. Two sections were cut from the specimen block along the longitudinal axis of the defect using an Exakt diamond blade bone saw (Exakt Technologies, Oklahoma, Okla.). Sections were ground using an Exakt microgrinder to 10-20 μm thickness and stained a modified Van Gieson bone stain for qualitative assessment of incorporation of the graft into the bone matrix, bone regeneration, and pathological assessment of the tissue response to the biomaterial. Sections were stained with a modified Van Gieson stain to provide vivid color contrast between bone (red), implant (opaque), osteoid (green), and fibrous tissue (blue) [data not shown].

Histomorphometric Analysis

Histological images were acquired using an Image Pro Imaging system (Media Cybernetics, Silver Spring, Md.) and a Nikon E800 microscope (AG Heinze, Lake Forest, Calif.), SpotRT digital camera (Diagnostic Instruments, Sterling, Heights, Mich.). Graft and host tissues were very similar, making automatic segmentation unreliable; so manual selection of graft tissues was required. Histomorphometric parameters measured included percent defect filled with graft, percent defect filled with bone, percent periosteal callus filled with graft, percent periosteal callus filled with bone, percent endosteal callus filled with graft, percent endosteal callus filled with graft, height of periosteal callus (mm) and height of endosteal callus (mm).

Histopathological Analysis

The regenerative tissue was evaluated for normality and cellular response to the graft material based on 55 slides using the following indices: presence of allograft plug (Y or N); inflammatory cells (0=none, 1=some, 2=many); extent of allograft resorption (0=none, 1=0-25%, 2=25-50%, 3=50-75%, 4=75-100%); surface with predominant allograft incorporation (E=endosteal, P=periosteal, B=both E&P, H=host bone, A=all surfaces); active osteoclast resorption of allograft (0=none, 1=some, 2=extensive); active osteoblastic bone formation (0=none, 1=some, 2=extensive); remodeling of new bone within allograft (0=100% woven bone, 1=some, primarily woven, 2=primarily lamellar, some woven, 3=completely remodeled to lamellar bone); presence of fibrous or cartilaginous tissue within defect (Y or N); integration of allograft with host bone (0=bone integration, 1=fibrous encapsulation, 2=mixed bone and fibrous integration); allograft plug extension (E=extension into medullary canal, P=extension from periosteal surface, C=contained within cortex); callus description (0=no callus, B=callus both periosteal and endosteal, E=endosteal callus, P=periosteal, X=cannot assess); larger callus, if applicable (E=endosteal, P=periosteal; size of endosteal callus (0=none or minimal, 1=0-25% of cortical thickness, 2=25-50% of cortical thickness, 3=50-75% of cortical thickness, 4=75-100% of cortical thickness;); size of periosteal callus (0=none or minimal, 1=0-25% of cortical thickness, 2=25-50% of cortical thickness, 3=50-75% of cortical thickness, 4=75-100% of cortical thickness); and remodeling of callus (0=100% woven bone, 1=some, primarily woven, 2=primarily lamellar, some woven, 3=completely remodeled to lamellar bone).

Biomechanical Testing

All biomechanical specimens were tested on the day of euthanasia. Once located and dissected on the Exakt saw, the specimens were tagged and wrapped in saline soaked gauze. Each specimen was cut to enable orientation of the allograft constructs perpendicular to the load. Briefly, the sagittal sections of tibia or metatarsal were cut transversely into distal and proximal ends each with two defects. The specimen was mounted on an alignment jig to enable perpendicular loading of the plug graft with respect to the cortical surface. Alignment was achieved by orienting the plug graft on the periosteal surface (which is easier to visualize) and, once aligned, the test specimen was flipped 180 degrees for push-out from the endosteal surface. The alignment jig (although still attached to the specimen) no longer provided support or orientation to the specimen during actual testing. Details on the procedures involved in aligning the allograft plugs for push-out are discussed below.

The host bone section was mounted on a 1 cm thick plywood support plate, which was approximately 19.5 cm by 13.5 cm with an 8 cm by 5.5 cm square section removed from the middle. The allograft plug was orientated approximately in the middle of the support plate hole and the host bone section was attached to the support plate with a drywall screw and hot glue.

A swivel plate with two jackscrew holding brackets was attached to the support plate with drywall screws. The assembly was then placed on a drill press table. A reaction plate and reaction plate holding assembly was inserted into the drill press chuck. The clearance of the hole in the reaction plate was adjusted to 1.5 mm, after the performance of preliminary testing, to simplify visual alignment of the allograft plug. A 3.5 mm diameter pilot rod was used to align the reaction plate hole to the allograft plug. The four jackscrews were used to raise lower and tilt the swivel plate to align the pilot rod with the allograft plug. The pilot rod was then removed and the reaction plate lowered to the host bone. Further visual inspection and fine adjustment was made using a mirror to look down the reaction plate hole and line up the allograft plug. The support plate was stabilized to the drill press table with two hold down clamp assemblies.

Four angle brackets were attached to the reaction plate and four headless screws were inserted into the plywood support plate. The reaction plate was raised and a paper strip with a circle of hot glue was placed around the allograft plug. The reaction plate was lowered on to the glue to create a bearing surface. Care was taken not to get any glue on the allograft plug or reaction plate hole. The reaction plate was attached to the support plate by hot gluing the headless screws to the angle brackets. When the glue dried, the support plate was removed from the swivel plate. The reaction plate assembly was turned over and attached to the OBRL servo-hydraulic testing system (MTS 858, Eden Prairie, Minn.) using another custom fixture.

After the specimen was oriented, a flat surface 3.5 mm diameter pin applied load to the allograft plug at a displacement rate of 2 mm/min with load and displacement data acquired at 100 Hz. Once the break load was reached, the testing was stopped.

After the allograft plug was pushed out, the host bone specimen was removed from the support plate. The second allograft plug was oriented in the middle of the support plate hole and the host bone was reattached to the support plate. The procedure as described above was repeated. After plugs were pushed out, pictures were taken of the specimen and it was wrapped in saline soaked gauze and placed in the freezer. The specimens were later removed from the freezer and the allograft plug hole was bisected with the Exakt Saw. Cortical bone thickness at the hole was measured with digital calipers.

The effects of allograft treatment on biomechanical (ultimate load, shear strength, and shear modulus), and histomorphometric (percent bone within defect, percent graft within defect, percent bone within periosteal callus, percent graft within periosteal callus, percent bone within endosteal callus, and percent graft within endosteal callus) analyses were determined using a one-way ANOVA. If significant effects of treatment were found, Duncan multiple comparisons were used to determine differences between treatments. All statistical analyses were performed using SAS statistical software (Cary, N.C.) at a significance level of $\alpha=0.05$.

No significant differences were detected between treatments for any of the biomechanical properties (ultimate force, shear strength, and shear modulus; all $p>0.05$). Slight trends toward greater ultimate load and shear strength during push out were seen for BMP treated allograft plugs, but these were not significant. However, although there was no difference in biomechanical results for the combination of BMP, there was synergistic effect as indicated above in the histomorphometric and histopathological studies.

Significantly more graft remained in the defect for the allograft and xenograft treatments ($p<0.005$), and significantly more percent bone was measured within defect for the ASD+BMP treatment group, while the allograft (untreated) group had significantly less bone within the defect than the other treatment groups ($p<0.001$). The allograft group had significantly less percent bone in periosteal callus compared to the other treatment groups ($p<0.05$). No significant differences between treatments were found for percent graft within periosteal callus ($p=0.88$) and percent graft and bone in endosteal callus ($p=0.18$ and $p=0.57$, respectively).

ASD+BMP showed the most consistent remodeling and plug incorporation with large portions of the allograft plug remodeled. Surface depressions appear to facilitate active bone formation and remodeling for ASD treatments. BMP-2 appears to aid osteoblast activity. Results with BMP with surface depressions indicate synergistic effect. As expected, the xenograft showed an immune response (i.e. inflammatory response).

Example 2

Following the protocol outlined in Example 1, Applicant photographed an osteograft according to the present invention. Photographs (not shown) showed undecalcified histology stained with modified Van Gieson stain to provide contrast between bone, implant, osteoid, and fibrous tissue. One photograph illustrated smooth, untreated cortical allograft bone used as an implant. Other photographs illustrated incorporation of osteograft formed of allograft bone with 1 mm diameter×1 mm deep surface pits. Photographs of the following were taken: (1) Pitted allograft, (2) Pitted allograft with recombinant human bone morphogenetic protein (rhBMP-2), and (3) pitted allograft plus demineralized bone matrix (DBM). Histomorphometrically, the combination of BMP and allograft surface depressions (ASD) showed synergistic effects to enhance bone remodeling and integration between host and graft tissue.

Example 3

Following the protocol of Example 1, allograft constructs were screened using an ovine cortical defect model. Different allograft surface treatments were compared using histopathological, histomorphometric, and biomechanical methods. By compiling data, it was possible to increase sample size and decrease variability. Histopathologically and histomorphometrically the combination of BMP and allograft with straight pits showed synergistic effects to enhance bone remodeling and integration between host and graft tissues.

There was not a statistically significant effect of treatment on the biomechanical responses measured. The results are represented in FIGS. 9 and 10.

Figure 9:
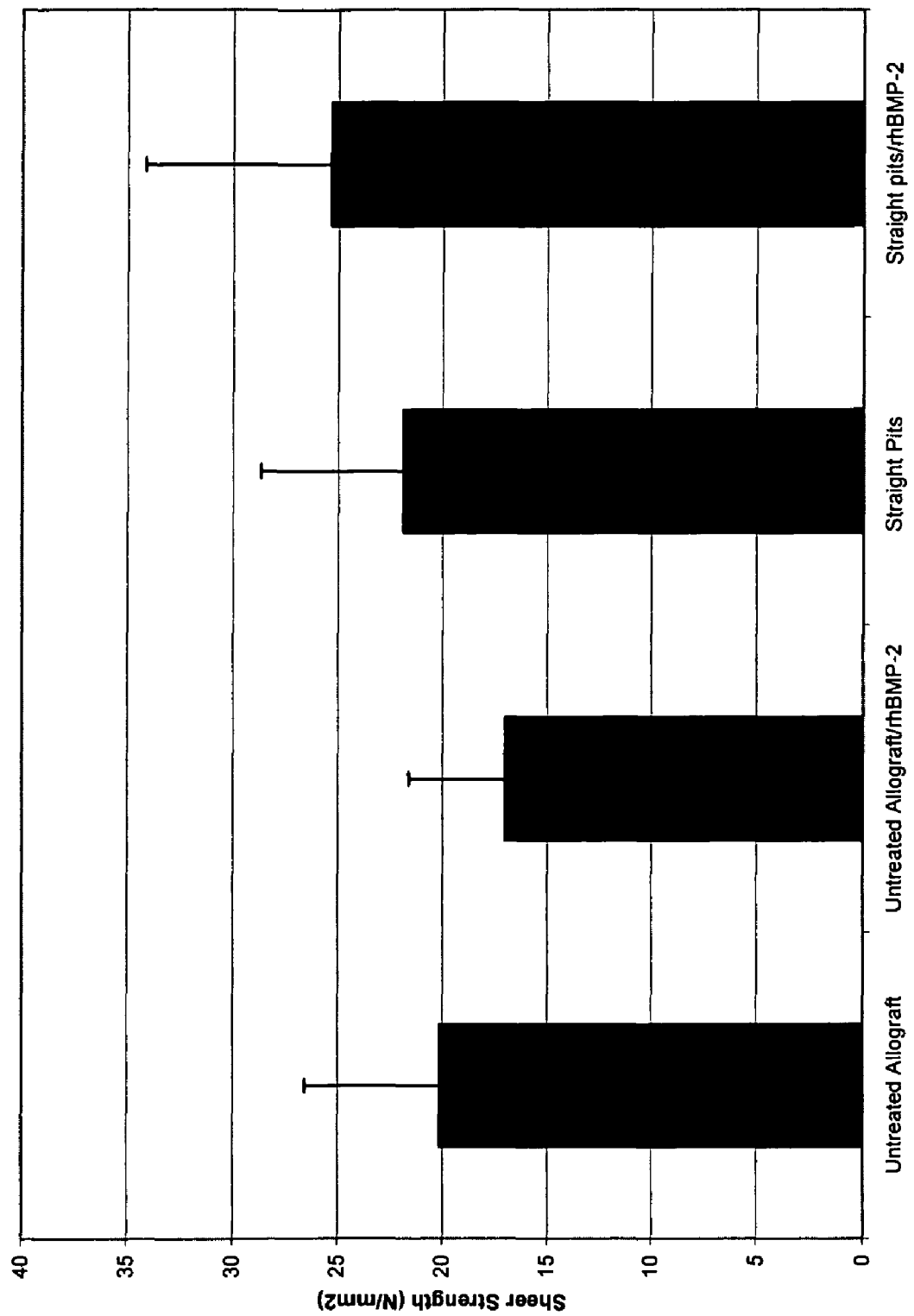
FIG. 9 is a bar graph which is measuring Shear Strength (N/mm$^2$) of an Untreated Allograft, an Untreated Allograft and rhBMP-2, an Allograft with Straight Pits and and Allograft with Straight Pits with rhBMP-2.

The bar graph of FIG. 9 indicated the shear strength (N/mm2) where Shear Strength=$F/(\pi DH)$; F=Ultimate Force (N); D=Outer diameter of cylindrical implant (4 mm in all cases); and H=Average transcortical bone interface thickness (mm). Tested and compared were an Untreated Allograft, an Untreated Allograft and rhBMP-2, an Allograft with Straight Pits and an Allograft with Straight Pits with rhBMP-2.

Figure 10:
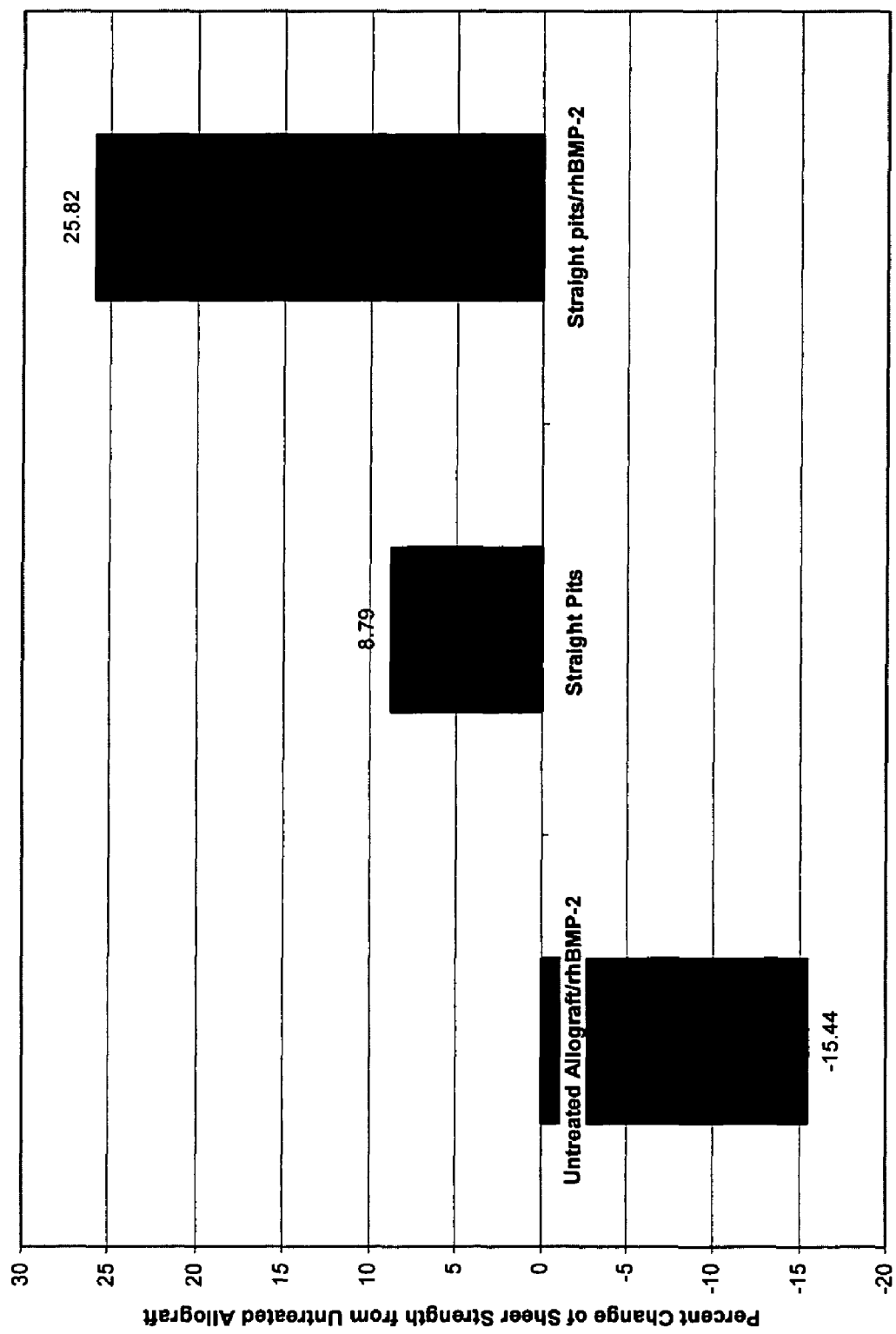
FIG. 10 is a bar graph showing the percent change of sheer strength of the Allograft with Straight Pits and the Allograft with Straight Pits with rhBMP-2 as compared to an Untreated Allograft.

The bar graph of FIG. 10 indicated the percent change of sheer strength of the Allograft with Straight Pits and the Allograft with Straight Pits with rhBMP-2 as compared to an Untreated Allograft. The Allograft with Straight pits and rhBMP-2 showed an increase in percent of sheer strength which was better than the other two samples.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claim.

We claim:

1. A delivery system comprising:
   a) an osteograft having at least one pit formed in at least one surface of the osteograft, the pit containing a bioactive agent comprising a LIM mineralization protein and a stem cell, and
   b) at least one plug inserted into the pit below the at least one surface of the osteograft, and the plug being a size smaller than the pit to form a reservoir in the pit and below the plug, and the plug is complementary to the shape of the pit, wherein the reservoir comprises a fluid and the pit has a diameter at the opening of the pit to height ratio such that surface tension will hold the fluid in the pit when the pit's opening is oriented downward.

2. The system of claim 1, wherein said osteograft has a plurality of pits on said surface.

3. The system of claim 2, where said plurality of pits are evenly spaced on the surface of the osteograft.

4. The system of claim 2, wherein all of said plurality of pits have a plug.

5. The system of claim 2, wherein a portion of said plurality of pits have a plug.

6. The system of claim 2, wherein said plug absorbs or adsorbs and retains the bioactive agent within said at least one pit.

7. The system of claim 2, wherein said at least one pit has a shape which promotes fluid retention.

8. The system of claim 7, wherein said shape increases retention of a bioactive agent through hydrostatic attraction.

9. The system of claim 7, wherein the shape of said at least one pit is selected from the group consisting of regular, linear, square, and combinations thereof.

10. The system of claim 2, wherein said at least one pit has an interior surface which is demineralized.

11. The system of claim 10, wherein said interior surface is demineralized by applying hydrochloric acid.

12. The system of claim 1, wherein the osteograft is an interbody fusion device.

13. The delivery system of claim 1, wherein the bioactive agent is provided in a modified-release microsphere.

* * * * *

UNITED STATES PATENT AND TRADEMARK OFFICE
CERTIFICATE OF CORRECTION

PATENT NO. : 8,092,548 B2  Page 1 of 1
APPLICATION NO. : 11/158924
DATED : January 10, 2012
INVENTOR(S) : McKay et al.

It is certified that error appears in the above-identified patent and that said Letters Patent is hereby corrected as shown below:

In Column 4, Line 1, delete "and and" and insert -- and --, therefor.

In Column 5, Line 44, delete "axisymetric" and insert -- axisymmetric --, therefor.

In Column 9, Line 21, delete "SpotRT" and insert -- SpoRT --, therefor.

In Column 12, Line 32, delete "claim." and insert -- claims. --, therefor.

In Column 12, Line 50, in Claim 3, delete "where" and insert -- wherein --, therefor.

Signed and Sealed this
Tenth Day of April, 2012

David J. Kappos
*Director of the United States Patent and Trademark Office*